United States Patent [19]

Yabe

[11] Patent Number: 4,741,327
[45] Date of Patent: May 3, 1988

[54] ENDOSCOPE HAVING BENT CIRCUIT BOARD

[75] Inventor: Hisao Yabe, Tokyo, Japan

[73] Assignee: Olympus Optical Co., Ltd., Tokyo, Japan

[21] Appl. No.: 38,019

[22] Filed: Apr. 14, 1987

[30] Foreign Application Priority Data

Apr. 30, 1986 [JP] Japan .................................. 61-98199

[51] Int. Cl.⁴ ................................................ A61B 1/06
[52] U.S. Cl. .......................................... 128/6; 358/98
[58] Field of Search ........................... 128/6, 4; 358/98

[56] References Cited

U.S. PATENT DOCUMENTS

| | | | |
|---|---|---|---|
| 4,573,450 | 3/1986 | Arakawa | 128/6 |
| 4,641,635 | 2/1987 | Yabe | 128/6 |
| 4,646,721 | 3/1987 | Arakawa | 128/6 |
| 4,646,723 | 3/1987 | Arakawa | 128/6 |
| 4,667,656 | 5/1987 | Yabe | 128/6 |
| 4,692,608 | 9/1987 | Cooper et al. | 128/6 X |

FOREIGN PATENT DOCUMENTS 60-25851 5/1985 Japan .

Primary Examiner—William H. Grieb
Attorney, Agent, or Firm—Ladas & Parry

[57] ABSTRACT

An endoscope of this invention includes a solid-state image sensor in a hard distal end portion of an insertion section thereof. A body cavity can be observed by utilizing the solid-state image sensor and an image reproduction apparatus. An objective optical system consisting of a plurality of objective lenses is arranged inside the distal end portion of the insertion section of the endoscope. One side surface of an optical element is in contact with the proximal end face of the objective optical system. The direction of the optical path of light reflected by the observed portion and incident on the optical element is changed into a direction substantially perpendicular to the optical axis of the optical element. A solid-state image sensor for converting light into an electrical signal is mounted on the other side surface of the optical element. A circuit board bent to surround the optical element includes an electrical circuit connected to the solid-state image sensor. Therefore, the space around the optical element can be efficiently utilized. In order to connect the electronic components and the bundle of signal lines to the circuit board, the diameter and length of the hard distal end portion of the endoscope need not be increased.

8 Claims, 4 Drawing Sheets

ENDOSCOPE HAVING BENT CIRCUIT BOARD

BACKGROUND OF THE INVENTION

A. Field of the Invention

The present invention relates to an endoscope comprising a solid-state image sensor in a distal end portion of an insertion section thereof.

B. Description of the Prior Art

An endoscope is known which has a solid-state image sensor in a distal end portion of an insertion section and allows observation of a body cavity in cooperation with the image sensor and an image reproduction apparatus.

A typical example of an endoscope with a solid-state image sensor is disclosed in Japanese Patent Disclosure (Kokai) No. 60-258515. The endoscope disclosed in this prior art comprises an objective optical system, a prism, and a solid-state image sensor. All beams reflected by a portion to be examined and incident on the objective optical system are reflected by the prism in a direction substantially perpendicular to the optical axis of the objective optical system and are guided to one side surface of the solid-state image sensor.

A flat circuit board is bonded to the other side surface of the solid-state image sensor. A large number of electronic components are mounted on the circuit board for amplifying an image signal sent from the solid-state image sensor, and for partially generating a solid-state image sensor driving pulse, and for adjusting a time lag between the solid-state image sensor driving pulse and an image output signal from the solid-state image sensor.

In a conventional endoscope having the structure described above, the electronic components having predetermined sizes are mounted on the flat circuit board, and the diameter of the distal end portion of the insertion section of the endoscope is inevitably increased.

In order to mount many electronic components on the circuit board, the board must be elongated along the axial direction of the insertion section. Therefore, the hard distal end portion of the insertion section of the endoscope is elongated accordingly.

When the distal end portion of the insertion section of the endoscope is enlarged and elongated, insertion of the insertion section into a body cavity causes great pain to the patient.

SUMMARY OF THE INVENTION

It is an object of the present invention to provide an endoscope wherein a circuit connected to a solid-state image sensor is mounted on a circuit board without enlarging or elongating the insertion section of the endoscope.

The above object is achieved by the following endoscope. The endoscope comprises an insertion section having a hard distal end portion. An objective optical system having a plurality of objective lenses is arranged in the distal end portion of the insertion section. The proximal end face of the objective optical system is bonded to one side surface of an optical element for changing a direction of an optical path of light reflected by a portion to be observed and incident on the objective optical system into a direction substantially perpendicular to the optical axis of the objective optical system. A solid-state image sensor is mounted on the other side surface of the optical element for converting the light into an electrical signal. A bent circuit board surrounding the optical element comprises an electrical circuit connected to the solid-state image sensor. The circuit board is arranged around the optical element.

In an endoscope according to the present invention, the space around the optical element can be stereoscopically utilized with high efficiency. In order to connect the electronic components and the bundle of signal lines to the circuit board, the hard distal end portion of the endoscope need not be enlarged or elongated.

DETAILED DESCRIPTION OF THE PREFERRED EMBODIMENTS

Preferred embodiments of the present invention will be described with reference to the accompanying drawings.

Figure 1:
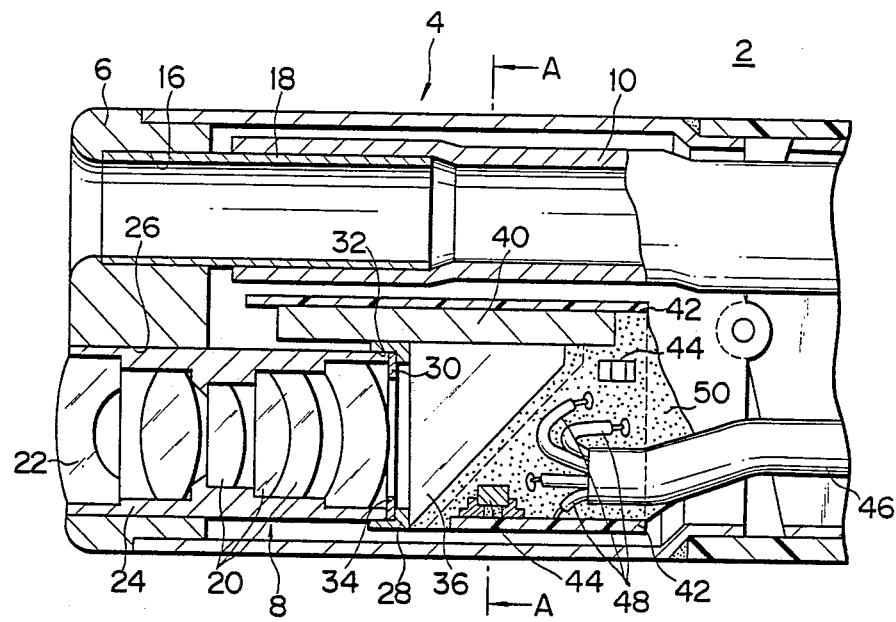
FIG. 1 is a longitudinal sectional view showing an endoscope according to a first embodiment of the present invention.
Figure 2:
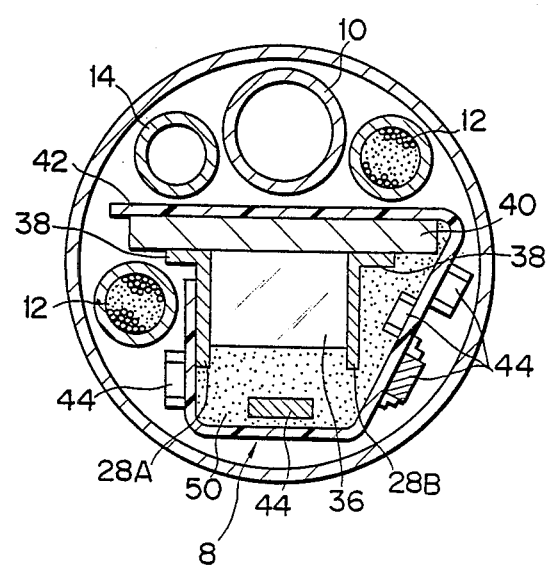
FIG. 2 is a cross-sectional view of the endoscope of FIG. 1, showing an insertion section cut away along the line A—A thereof.

FIGS. 1 and 2 show an insertion section of an endoscope according to a first embodiment of the present invention. Insertion section 2 of the endoscope shown in FIG. 1 has hard distal end portion 4. The distal end of portion 4 has distal end member 6. Objective optical system or image pickup system 8, channel 10 for a treatment tool, a pair of light guide fiber elements 12, and air/water supply tube 14 are housed inside distal end portion 4. As shown in FIG. 1, channel 10 is connected through connecting pipe 18 to first mounting hole 16 formed in distal end member 6. The pair of light guide fiber elements 12 are optically connected to an illumination window (not shown) formed in distal end member 6. Supply tube 14 is connected to a nozzle (not shown) mounted on distal end member 6.

Figure 3:
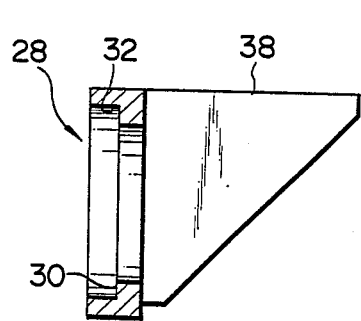
FIG. 3 is a longitudinal sectional view of a prism frame according to the first embodiment.
Figure 4:
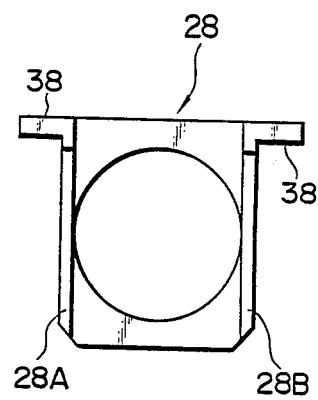
FIG. 4 is a rear view of the prism frame.
Figure 5:
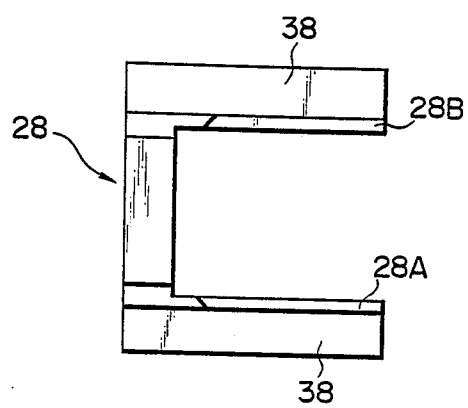
FIG. 5 is a bottom view of the prism frame.

Objective optical system 8 comprises lens frame 24. A large number of objective lenses 20 are built into lens frame 24. Cover lens 22 is mounted in the distal end portion of frame 24. The outer surface of the distal end portion of lens frame 24 is fitted in second mounting hole 26 formed in distal end member 6. Prism frame 28 is mounted at the rear end portion of frame 24. As shown in FIGS. 3 to 5, prism frame 28 has an inclined substantially U-shaped upper surface. Side portions 28A and 28B are formed at two sides, respectively. Fitting hole 32 having step 30 is formed in the front end portion. The rear end portion of lens frame 24 is fitted in hole 32. Spacer 34 is inserted between the step 30 and the rear end face of lens frame 24. As a result, the position of frame 24 is set. If spacer 34 is replaced with another spacer having a thickness different from that of spacer 34, the position of frame 28 can be adjusted.

As shown in FIG. 2, rectangular prism 36, as an optical element, is bonded and fixed between side portions 28A and 28B of prism frame 28. Prism 36 reflects all beams reflected by the observed portion passing through objective lenses 20. The beams are reflected at a right angle. Solid-state image sensor 40 is arranged in a propagation direction of the reflected beams. One side of sensor 40 is bonded and fixed to a pair of collars 38 formed at the upper ends of side portions 28A and 28B of frame 28. Since collars 38 are formed in prism frame 28, solid-state image pickup sensor 40 can be firmly fixed to frame 28. Frame 28 is aligned by axial abutment with frame 24, and objective optical system 8 is then focused. With this structure, therefore, as compared with a structure wherein prism frame 28 is slidably mounted to lens frame 24 and the lens is focused, cluttering in the area between the prism frame and the lens frame can be greatly reduced. In addition, the overall distance between the prism frame and the lens frame can be shortened.

As shown in FIG. 2, one end of flexible circuit board 42, made of a synthetic resin, is adhered and fixed to the other side surface of solid-state image sensor 40. Circuit board 42 is bent and surrounds prism 36. The other end of board 42 is connected and fixed to side portion 28A of prism frame 28. Electronic components 44 such as transistors, ICs, and capacitors are mounted on board 42 for amplifying and processing an image signal output from image sensor 40. A bundle of signal lines 46 is inserted in the space defined by circuit board 42. The ends of the bundle of signal lines 46 are located near prism 36, and single lines 48 extending from the end face of the bundle are folded backward and electrically connected to circuit board 42. Adhesive 50 is filled in the space defined by circuit board 42 and assures rigid electrical connections between lines 48 and circuit board 42. In this embodiment, lines 48 are folded backward, and thus the space near the connecting portion can be reduced. Hard distal end portion 4 of the endoscope can be shortened and a relatively small amount of adhesive is filled in this space.

Beams reflected by the observed portion are converted into an electrical image signal by solid-state image sensor 40. The electrical signal is amplified, and the amplified signal is sent to an image reproduction apparatus (not shown) through the bundle of signal lines 46.

Circuit board 42 having electronic components 44 is bent to surround prism 36 at the distal end portion of the endoscope according to the present invention. As compared with the conventional endoscope having a flat circuit board, a larger space of circuit board 42 can be assured. Therefore, a three-dimensional mounting density of electronic components 44 and the bundle of signal lines 46 can be increased to reduce the diameter and length of hard distal end portion 4. In the distal end portion of the endoscope, circuit board 42 is bent to surround prism 36, and the space which was not utilized in the conventional arrangement is effectively utilized. The diameter and length of hard distal end portion 4 can be reduced.

Figure 6:
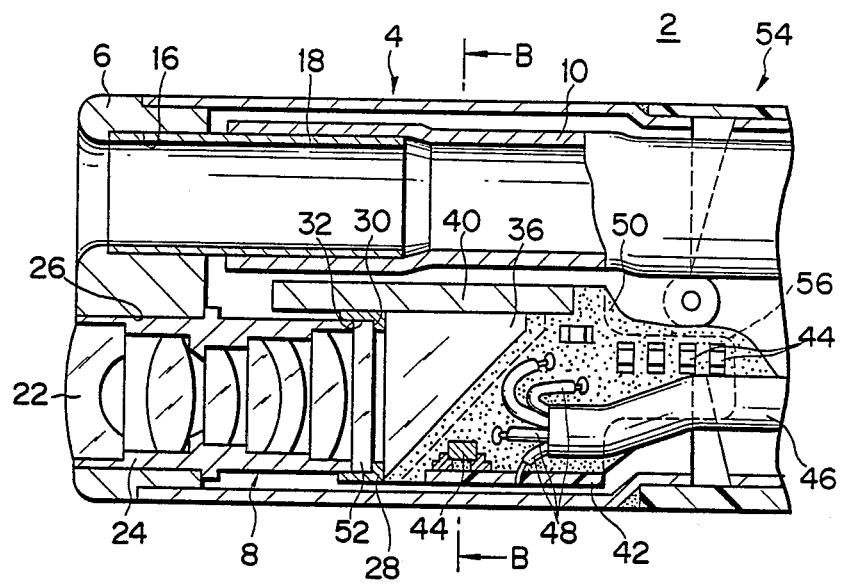
FIG. 6 is a longitudinal sectional view of an endoscope according to a second embodiment of the present invention.
Figure 7:
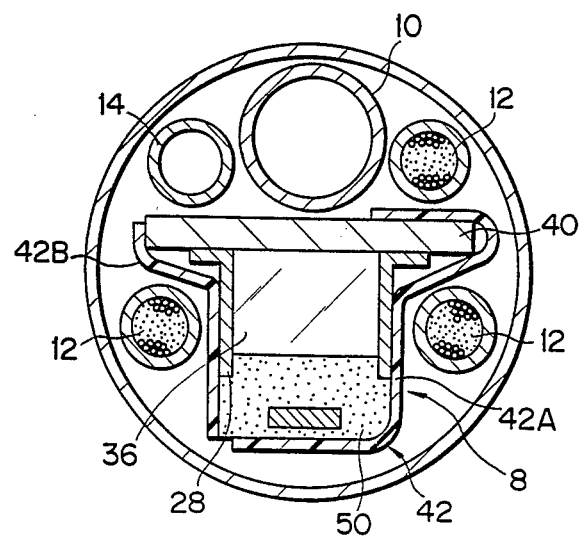
FIG. 7 is a cross-sectional view of the endoscope of FIG. 6, showing an insertion section cut away along the line B—B thereof.

A second embodiment of the present invention is shown in FIGS. 6 and 7. In this embodiment, circuit board 42 is divided into first circuit board portion 42A and second circuit board portion 42B. A portion of circuit board 42 between solid-state image sensor 40 and channel 10 can be omitted. Therefore, at the endoscope distal end portion having a predetermined outer size, the diameter of channel 10 can be increased by the thickness of the circuit board. In this embodiment, glass plate 52 is used in place of spacer 34 at a coupled portion between lens frame 24 and prism frame 28. By changing the thickness of glass plate 52, objective optical system 8 can be focused. Circuit board 42 according to the second embodiment comprises portion 56 extending into bending portion 54, as shown in FIG. 6. Therefore, the area for circuit board 42 can be further increased, as compared with the first embodiment. Extended portion 56 is preferably formed near the center of insertion section 2 so as not to interfere with bending of portion 54.

Figure 8:
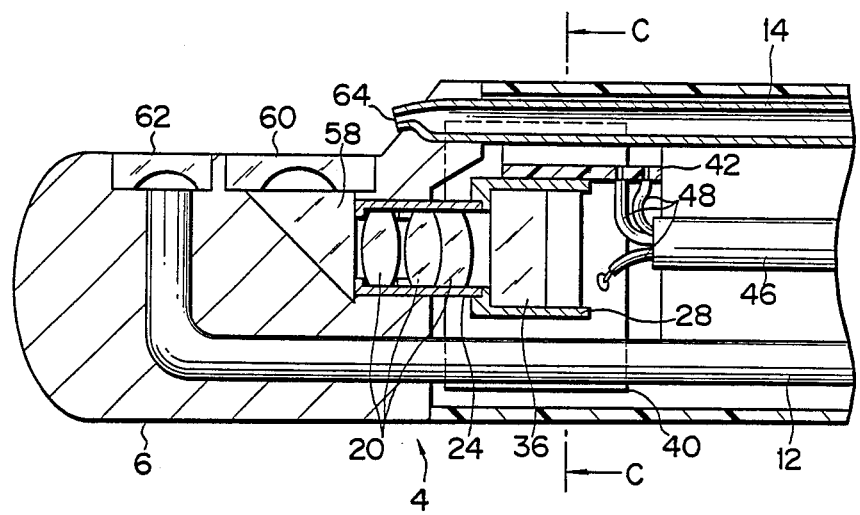
FIG. 8 is a longitudinal sectional view of an endoscope according to a third embodiment of the present invention.
Figure 9:
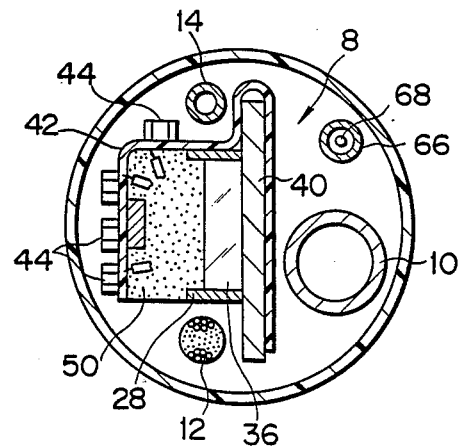
FIG. 9 is a cross-sectional view of the endoscope of FIG. 8, showing an insertion section cut away along the line C—C thereof.

A third embodiment of the present invention is shown in FIGS. 8 and 9. In this embodiment, a flexible circuit board as in circuit board 42 is applied to the distal end portion of the endoscope of a side observation type. In the distal end portion of the endoscope, objective lenses 20 held in lens frame 24 are optically coupled to observation window 60 through objective prism 58. In this embodiment, illumination window 62 is optically coupled to light guide fiber elements 12. Air/water supply tube 14 is connected to nozzle 64 to supply a liquid thereto. Wire 68 is inserted in guide tube 66 of FIG. 9 to open forceps inserted in channel 10. In the endoscope of a side observation type, the same effect as in the first embodiment can be obtained by use of a flexible circuit board.

In each embodiment described above, circuit board 42 can be a flexible-rigid printed board. Electronic components 44 or the bundle of signal lines 46 can be mounted on the rigid portion of this printed board.

Alternatively, in each embodiment, circuit board 42 can be a mold circuit board made of a synthetic resin by injection molding.

What is claimed is:

1. An endoscope comprising:
   an insertion section having a hard distal end portion;
   an objective optical system arranged in said distal end portion of said insertion section;
   an optical element one side surface of which is in contact with a proximal end face of said objective optical system, said optical element being adapted to change a direction of an optical path into a direction substantially perpendicular to an optical axis of said objective optical system;
   a solid-state image sensor mounted on the other side surface of said optical element, said image sensor being adapted to convert light incident on said objective optical system into an electrical signal; and
   a circuit board having an electrical circuit connected to said solid-state image sensor, said circuit board being bent to surround said optical element.

2. An endoscope according to claim 1, wherein said circuit board comprises a flexible circuit board.

3. An endoscope according to claim 1, wherein said circuit board is made of a synthetic resin.

4. An endoscope according to claim 1, wherein said optical element comprises a prism.

5. An endoscope according to claim 4, further comprising a prism frame arranged between said objective optical system and said prism, said prism frame being adapted to have an inclined substantially U-shaped member with a space for housing said prism therein.

6. An endoscope according to claim 5, further comprising spacing means arranged between said objective optical system and said prism frame to focus said objective optical system.

7. An endoscope according to claim 1, wherein said circuit board comprises first and second divided circuit board portions, one end of each of said first and second circuit board portions being connected to a corresponding edge portion of said solid-state image sensor.

8. An endoscope according to claim 1, further comprising an observation window formed on one side surface of said insertion section, and a second optical element arranged between said observation window and said optical element, said second optical element being adapted to supply a side vision to said solid-state image sensor, thereby providing an endoscope of a side observation type.

* * * * *